US005614528A

United States Patent [19]

Jones et al.

[11] Patent Number: 5,614,528
[45] Date of Patent: *Mar. 25, 1997

[54] COMPOSITIONS AND METHODS FOR INHIBITING THE FORMATION OF CHLORAMINES AND TRIHALOMETHANES IN AQUEOUS MEDIA

[75] Inventors: Ronald L. Jones, Norcross; Henry D. Caughman, Lithonia; Susan M. Shelor, Stone Mountain; Ellwood L. Lines, Jr., Atlanta, all of Ga.

[73] Assignee: Bio-Lab, Inc., Decatur, Ga.

[ * ] Notice: The term of this patent shall not extend beyond the expiration date of Pat. No. 5,498,415.

[21] Appl. No.: 324,389

[22] Filed: Oct. 17, 1994

Related U.S. Application Data

[63] Continuation of Ser. No. 38,166, Mar. 29, 1993, abandoned, which is a continuation-in-part of Ser. No. 755,822, Sep. 6, 1991, abandoned.

[51] Int. Cl.$^6$ ............................. A01N 25/22; A61L 9/01
[52] U.S. Cl. ..................... 514/258; 514/241; 514/387; 514/389; 424/76.1; 424/76.8; 424/661; 504/155; 504/156
[58] Field of Search ..................... 424/661, 76.1, 424/76.8; 514/241, 387, 389, 258; 548/304, 308; 504/124, 121, 129, 130, 131, 132, 133, 134, 139, 141, 151, 152, 155, 241

[56] References Cited

U.S. PATENT DOCUMENTS

| | | | |
|---|---|---|---|
| 2,731,472 | 1/1956 | Reibnitz | 260/309.7 |
| 2,789,078 | 4/1957 | Trusler | 424/358 |
| 2,863,800 | 12/1958 | Gottfried | 514/389 |
| 2,988,471 | 6/1961 | Fuchs et al. | 424/661 |
| 3,019,075 | 1/1962 | Rosen et al. | 8/108 |
| 3,071,591 | 1/1963 | Paterson | 260/309.7 |
| 3,165,521 | 1/1965 | Slezak et al. | 71/67 |
| 3,187,004 | 6/1965 | Slezak et al. | 548/304 |
| 3,201,311 | 8/1965 | Antonides et al. | 514/241 |
| 3,252,901 | 5/1966 | Zettler | 210/62 |
| 3,342,674 | 9/1967 | Kowalski | 514/241 |
| 3,445,383 | 5/1969 | Horvath | 210/62 |
| 3,629,408 | 12/1971 | Horvath | 424/149 |
| 3,647,523 | 7/1972 | Horvath et al. | 117/100 |
| 4,187,293 | 2/1980 | Nelson | 424/149 |
| 4,780,216 | 10/1988 | Wojtowicz | 424/661 |
| 5,000,869 | 3/1991 | Dittert | 252/174.13 |
| 5,015,643 | 5/1991 | Jones et al. | 424/661 |
| 5,498,415 | 3/1996 | Jones | 424/409 |

OTHER PUBLICATIONS

S.D. Worley and D.E. Williams, "Halamine Water Disinfectants," CRC Critical Reviews In Environmental Control, vol. 18, Issue 2 (1988).

Primary Examiner—Allen J. Robinson
Assistant Examiner—Brian G. Bembenick
Attorney, Agent, or Firm—Woodard, Emhardt, Naughton Moriarty & McNett

[57] ABSTRACT

Compositions and methods are disclosed for sanitizing aqueous media, which combine a chlorine-source composition and a glycoluril-source composition. The compositions are added together or separately, continuously or periodically, and by any of a variety of methods. The glycoluril compound stabilizes the chlorine and prolongs its useful life as a microbicidal agent while additionally reducing the formation of chloramines, trihalomethanes and odors.

22 Claims, 5 Drawing Sheets

COMPOSITIONS AND METHODS FOR INHIBITING THE FORMATION OF CHLORAMINES AND TRIHALOMETHANES IN AQUEOUS MEDIA

REFERENCE TO RELATED APPLICATIONS

This application is a continuation of application Ser. No. 08/038,166, filed Mar. 29, 1993, now abandoned, which is a continuation-in-part of U.S. patent application Ser. No. 07/755,822, filed Sep. 6, 1991 by the same inventive entity, and entitled COMPOSITIONS AND METHODS FOR CONTROLLING THE GROWTH OF MICROBIALS IN AQUEOUS MEDIA (now abandoned).

BACKGROUND OF THE INVENTION

1. Field of the Invention

The present invention relates generally to disinfectant systems for swimming pools, spa water, cooling tower water and other aqueous media. More particularly, the invention relates to systems utilizing chlorine as a disinfectant, and to compositions and methods for inhibiting the production of chloramines and trihalomethanes in such systems.

2. Background

It is known to the art that swimming pools, spa water, cooling tower water and other aqueous media require chemical sanitation. Chlorine, in various forms, is the most widely used chemical for this purpose, being both economical and highly effective for bacteria and algae control. The use of chlorine presents certain problems however, including the need to stabilize the chlorine to prevent its depletion over an extended period of time.

In addition, it is known that eye and skin irritation may be caused by swimming pools and/or spas using chlorine-based sanitation systems. Also, undesirable odors may result when such sanitation systems are employed. The most common of these problems is caused by the formation of irritating and odorous dichloramines and possibly trichloramines. These compounds may be formed in reactions with organic or inorganic nitrogen-containing compounds such as urea, creatinine, uric acid, amino acids, etc., which may be introduced into the water by bacteria, algae, insects, air or swimmers.

Not only do chloramines have disagreeable odor and irritational properties, they are much less effective as biocides than hypochlorous acid. In particular, chloramines are reported to be only 1/80th as biocidally active as free available chlorine.

It is known to the art that chloramine formation is promoted when the pH of the water is at least slightly acidic. Because it is not uncommon for swimming pool waters to become acidic, chloramines form easily therein. In addition, the presence of nitrogen-containing compounds in swimming pool water promotes chloramine formation since favorable nitrogen-to-chlorine ratios commonly exist in such waters.

The production of chloramines in aqueous media has been inhibited in prior art systems by superchlorination—the application of a "shock" dose of free available chlorine (e.g., 10 ppm) to pool water to oxidize organic and inorganic nitrogenous and other wastes from the water. This method does not extend the useful life of the chlorine, and may cause eye and skin irritation problems of its own.

It is also known that trihalomethanes, such as chloroform, may be present in swimming pool waters treated with conventional chlorine-source compositions. These compounds not only cause eye and skin irritations, at certain concentrations they are toxic by inhalation. Even at concentrations insufficient to be toxic, trihalomethanes have distinctive odors which are objectionable for certain applications.

A need therefore exists for a method of inhibiting the formation of chloramines, trihalomethanes and odors in aqueous systems while stabilizing the chlorine in the water. The present invention addresses that need.

SUMMARY OF THE INVENTION

Briefly describing the present invention, there are provided methods for reducing or eliminating odors in swimming pool water by maintaining concentrations of about 1–100 ppm glycoluril in the water. Preferably, 5–20 ppm glycoluril is maintained. Another aspect of the present invention is to provide compositions and methods to inhibit the formation of trihalomethanes and chloramines in aqueous systems.

Further objects and advantages of the present invention will be apparent from the following description.

DESCRIPTION OF THE PREFERRED EMBODIMENT

Figure 1:
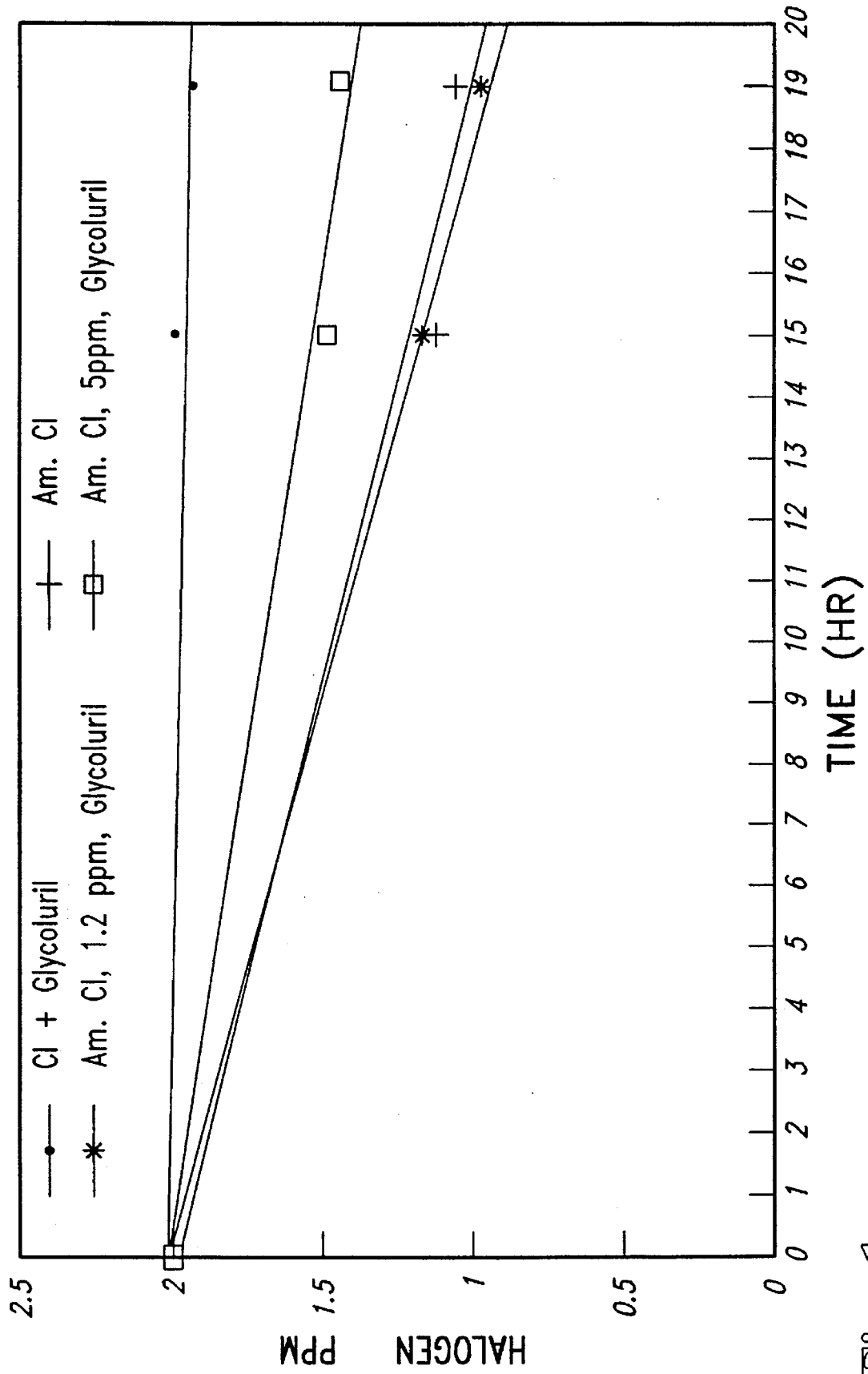
FIG. 1 shows chloramine volatility over time in the presence of ammonia, with and without glycoluril.

For the purposes of promoting an understanding of the principles of the invention, reference will now be made to the preferred embodiment of the invention and specific language will be used to describe the same. It will nevertheless be understood that no limitation of the scope of the invention is thereby intended, such alterations, modifications and further applications of the principles of the invention being contemplated as would normally occur to one skilled in the art to which the invention relates.

The use of chlorine as a disinfectant for swimming pool water, cooling tower water and other aqueous media has been well known for many years. In these environments, chlorine compounds are continuously or periodically added to the water to maintain a microbicidal concentration of chlorine. Without periodic addition, the effective chlorine concentration in the water will decrease due to dissipation, reaction, conversion into unusable forms, etc. In accordance with past methods, the useful life of added chlorine has been undesirably short, and there has remained an unsatisfied need for extending the effective life of added chlorine compounds.

The present invention provides compositions, systems and methods for extending the useful life of chlorine provided to aqueous media for disinfecting purposes, while also reducing the production of trihalomethanes and chloramines. In particular, the present invention utilizes the activity of glycoluril as a stabilizer for chlorine in an aqueous environment. Addition of the glycoluril and chlorine compositions may be at the same or different times, continuous or periodic, and by any of a variety of addition methods. The presence of the glycoluril at a stabilizing concentration suited to the chlorine concentration will result in an extended effective life for the chlorine in a state suitable for microbicidal activity. For example, the half-life for trichloro-s-triazinetrione (TCCA) in a given system is about 6–7 hours, whereas use of glycoluril in the system extends the half-life to about 20–25 hours.

The present invention utilizes a glycoluril-source composition that provides glycoluril to stabilize and prolong the useful life of the chlorine while inhibiting the formation of chloramines and trihalomethanes and the odors which may be caused thereby. Glycoluril-source compositions useful with the present invention include any composition which will contribute a glycoluril compound compatible with and useful for stabilizing the chlorine, and suitable for the aqueous media being treated. Substitution on the glycoluril is not critical, provided that the substituents do not interfere with the utility of the glycoluril in the manner described herein.

As used herein, the term "glycoluril" encompasses a compound which includes the basic formula:

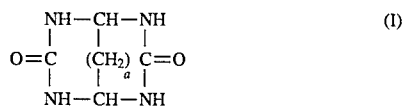

(I)

in which a is either 0 or 1. As used herein, the compound consisting solely of the structure shown in formula (I) is referred to as "unsubstituted glycoluril". In addition to the unsubstituted glycoluril (I), useful glycoluril-source compositions include the chloro, alkyl and phenyl substituted glycolurils. The term glycoluril thus includes compounds of the foregoing basic structure (I), as well as compounds including substituents such as alkyl, phenyl and chloro groups at available bonding sites. Bromo-substituted glycolurils may also be useful in certain applications, although the presence of the bromine substituent may interfere in some systems with the utility of the glycoluril as a chlorine stabilizer.

More specifically, preferred glycoluril-source compositions include glycolurils having the following structure:

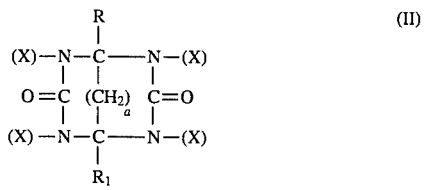

(II)

in which R and $R_1$ are independently selected from the group consisting of hydrogen, lower alkyl radicals of from 1 to 4 carbon atoms, and phenyl; each X is either hydrogen, chlorine or bromine; and a is either 0 or 1. It is preferred that R and $R_1$ be either hydrogen or methyl, as alkyl radicals with longer carbon lengths render the glycolurils less soluble in water.

The chlorine concentration in the aqueous media may be obtained from any suitable source which provides hypochlorous acid (HOCl) to the water. Chlorine-source compositions may include both inorganic and organic materials. Useful inorganic materials include molecular chlorine, lithium hypochlorite (LiOCl), calcium hypochlorite ($Ca(OCl)_2$), sodium hypochlorite (NaOCl) and hypochlorous acid (HOCl). Organic sources may include, for example, bromochlorodimethylhydantoin (BCDMH), dichlorodimethylhydantoin (DCDMH) or compositions based on cyanuric acid, such as sodium or potassium dichloro-s-triazinetrione or trichloro-s-triazinetrione (TCCA). These compounds are readily available in commercial form. TCCA, for example, is available from several different suppliers, including Monsanto Chemical Co. under the name ACL-90. The most preferred composition is TCCA. However, it will be appreciated that time chlorine source is not critical to the present invention, provided that the source is compatible with the aqueous media system being treated and is stabilized by the glycoluril compound which is utilized.

A wide variety of aqueous media may be treated by the present invention. In general, any aqueous media which is effectively treated with chlorine, and which is compatible with the described chemicals, can be treated. Typical systems for which the present invention is useful include swimming pools, spas, hot tubs and health related baths, decorative fountains, recirculating water cooling systems, dehumidifier systems, ponds, reservoirs and waste water systems.

The concentrations of glycoluril and chlorine will vary depending on the aqueous media being treated. An advantage of the present invention is that the level of glycoluril can be readily matched to the desired chlorine concentration effective for the given aqueous system. The selected glycoluril level will facilitate maintaining the desired microbicidal level of the chlorine in the water.

The appropriate concentrations of the chlorine, and therefore of the glycoluril, will also differ based upon the conditions attendant to the aqueous media. For example, effective levels may differ based upon such factors as the extent and nature of activity needed, the presence of other treatment chemicals, and conditions of use such as temperature, amount of sunlight, pH and the like. Generally, any factors which affect the stability of the chlorine will have an impact on the desired glycoluril levels. The present invention contemplates that the desired level of chlorine and of glycoluril can be readily determined by one of ordinary skill in the art without undue experimentation, and specific concentrations therefore are not specified herein for each variety of treatable aqueous systems.

The level of glycoluril in the water is that which provides an effective concentration of glycoluril to usefully stabilize the chlorine present in the system while inhibiting the formation of chloramines, trihalomethanes and odors. Typical concentrations of glycoluril effective as described will range from about 0.1 to about 40.0 ppm. More preferably, the glycoluril is present at a concentration of from about 5.0 to about 20.0 ppm, although concentrations of up to about 100 ppm may be used.

One instance in which it may be desirable to provide levels of glycoluril as high as 100 ppm is the initial treatment of a pool. In this way the level of glycoluril will remain at an effective level for a prolonged period of time. In addition, such high levels of glycoluril may be used with particularly high levels of chlorine.

The concentration of the chlorine in the water is that which provides an effective level of chlorine for the degree of microbicidal activity desired for the given aqueous media. The term total available chlorine is used herein to include both free chlorine and combined chlorine. Typically, a suitable concentration of total available chlorine will be in excess of about 1.0 ppm, and preferably will range from about 1.0 to about 5.0 ppm in the water. This is true, for example, in the case of swimming pool water. By way of comparison, the desired total available chlorine level in cooling tower water may differ, ranging from about 1.0 to about 10.0 ppm total available chlorine.

One aspect of the present invention advantageously uses two separate compositions, one primarily providing the chlorine and the other primarily providing the glycoluril. The overall effect is that the glycoluril is maintained at a level which both prolongs the useful life of the chlorine in the system and reduces the formation of chloramines, trihalomethanes and odors. Although certain forms of glycoluril-source compositions may include chlorine which will be contributed to the water, such forms of glycoluril are contemplated in the present invention as primarily stabilizing compositions. Indeed, the amount of chlorine which can be added to the water through a chlorinated form of glycoluril is typically either insufficient, or would require the use of amounts of chlorinated glycoluril which are otherwise undesirable.

The glycoluril and chlorine compositions may be administered to the aqueous media in any manner effective to provide the desired concentrations of each compound. The glycoluril and chlorine may be added to the water either together or separately, and either periodically or continuously. The methods of application may vary with the aqueous systems being treated, and the conditions of use pertinent thereto. In general, however, the methods are restricted only by the need to maintain effective levels of the glycoluril and chlorine as described, and may be any suited to the physical forms and particular compounds employed. Existing disinfectant systems using chlorine contemplate various methods for maintaining a desired level of the chlorine in an aqueous system. The present invention is advantageous in that it may be readily adapted for use with a wide variety of such existing water treatment systems.

Typical methods of addition known in the art are broadcast and erosion methods. Broadcasting refers to a direct addition of the chemical to the aqueous media in solid, typically granular, or liquid form. Compositions useful in the present invention may be readily prepared in forms and concentrations convenient for broadcast application.

In the erosion method, compositions are fabricated into a solid-form material which is contacted with the water in a manner to effect a relatively slow erosion of the solid material, thus gradually releasing the composition into the water. The composition to be added is formed or compressed into solid forms, such as tablets, sticks, pucks and other shapes, typically by a hydraulic or mechanical press. The solid-form materials may include inert fillers, such as sodium chloride or boric acid, that assist in the tabletting process. The solid material may also contain other ingredients such as tabletting aids, e.g., mold release agents, binders, corrosion inhibitors, scale inhibitors and other components known to those skilled in the art.

Erosion methods are commonly employed in the prior art for introducing chlorine-source compositions into swimming pools, for example. The chlorine composition, in solid form, is placed into a release device through which water is circulated to erode the solid material. In the case of a swimming pool, the tablet, stick or puck can be placed into a skimmer basket, in-line or off-line feeders, or a floating release device. While erosion may also be used for the glycoluril, it has been found that at least certain forms and types of glycoluril are not well suited to introduction by continuous erosion methods, because for these forms the erosion method provides insufficient levels of glycoluril in the water.

The glycoluril-source and chlorine-source compositions may be provided either as two separate materials or as a physically combined product, depending on the form and intended manner of addition of the products. The provision of separate materials is preferred since the preparation of the compositions is thereby made simpler. Also, the methods and compounds for adding the chlorine and the glycoluril are more flexible, for example permitting the use of liquid chlorine with a granular glycoluril composition, or permitting the continuous erosion addition of the chlorine and a periodic broadcasting of the glycoluril composition. The separate addition further enables the user to independently control the concentrations of the two compounds, which will be particularly useful if the water conditions result in a disparate depletion of one compound compared to the other.

One particular method of maintaining the desired levels of chlorine and glycoluril is to provide a continuous addition of chlorine to the water, coupled with a periodic broadcast addition of the glycoluril compound. Additive glycoluril-source compositions can be readily formulated to provide the desired levels of glycoluril in water upon addition of prescribed amounts of material at indicated time intervals. For example, granular forms of the compositions may be readily prepared which give desired concentrations of glycoluril when added to the water at intervals ranging from daily to every week or two. Naturally, the frequency of addition will depend on the conditions to which the water is subjected, and also on the amount, concentration and type of glycoluril-source composition being added.

In a particular embodiment, the foregoing method may be enhanced by using as the chlorine source a mixture of a chlorine compound and a glycoluril compound in a physical combination which facilitates sustained release of the chlorine compound into the water. Thus, a tablet or stick form of chlorine-source material may be formulated which also includes a percentage of glycoluril. The glycoluril is formulated with the chlorine-source compound in the solid tablet or stick because it has been found that this will slow the erosion rate for the solid material. This in turn extends the life of the solid material and reduces the frequency with which the tablets or sticks need to be replaced. Consequently, the chlorine is added to the aqueous system at a controlled and uniform rate over a longer period of time. The tablet in this method will also contribute a certain amount of glycoluril to the water, but the desired level of glycoluril may not be primarily obtained from this source. Instead, a glycoluril-source compound is also otherwise added into the water, such as by periodic broadcasting, to bring up and maintain the level of glycoluril in the water as desired.

According to this particular approach, the solid form tablets or sticks are formulated to include both chlorine and glycoluril source compounds. The chlorine compound is preferably selected from the group consisting of calcium hypochlorite, lithium hypochlorite, sodium dichloro-s-triazinetrione, potassium dichloro-s-triazinetrione, and trichloro-s-triazinetrione, and is present in an amount of from about 50.0% to about 99.99% by weight. The glycoluril-source composition is preferably selected from the group consisting of glycoluril, alkyl-substituted glycoluril, phenyl-substituted glycoluril, and chloro-substituted glycoluril, and is present in an amount of from about 0.01% to about 50.0% by weight. Further discussion of such compositions and their advantages is contained in the copending U.S. patent application Ser. No. 652,983, filed Feb. 11, 1991, and hereby incorporated by reference.

In accordance with this method, a particular embodiment of the solid-form chlorine material comprises approximately 50–99.99% by weight of trichloro-s-triazinetrione and 0.01–50% by weight of glycoluril. In a related embodiment, the solid-form material includes approximately 50–99.9% by weight of trichloro-s-triazinetrione, 0.01–50% by weight of glycoluril and 0–20% by weight of an alkali bromide salt. A preferred composition is 80–98% trichloro-s-triazinetrione (TCCA) and 2–20% glycoluril, or 70–90% trichloro-s-triazinetrione (TCCA), 5–10% sodium or potassium bromide salt, and 5–20% glycoluril. Another preferred mixture is 75–90% trichloro-s-triazinetrione, 5–10% potassium bromide and 5–20% glycoluril. The preferred glycolurils are unsubstituted glycoluril (I) and the chloroglycolurils, such as dichloroglycoluril and tetrachloroglycoluril. For most applications, glycoluril is preferred.

By way of particular example, the present invention is well suited to use in the treatment of swimming pool water. Current systems provide for the addition of chlorine to maintain certain accepted levels, typically 1 to 5 ppm of total available chlorine in the water. The present invention may be directly adapted for use in the variety of prior art systems which utilize chlorine as a disinfectant by maintaining in such systems the indicated levels of glycoluril effective to both stabilize the chlorine and reduce the formation of chloramines, trihalomethanes and odors. The glycoluril also may be used with various other treatment chemicals typically used in such systems, such as algicides, clarifiers and the like.

In addition, it is a feature of the present invention that the compositions may be readily formulated so as to be specifically adapted for use in swimming pools or other water systems. Swimming pool chemicals, for example, are typically constituted to require the addition of convenient, prescribed amounts on a periodic basis, usually weekly. The chemicals utilized in the present invention can be formulated on this basis. More preferably, one aspect of the present invention prolongs the useful life of the chlorine to the point that the frequency of addition of chemicals may be extended beyond the usual weekly basis, perhaps to once every two weeks or longer.

In a typical swimming pool application, the process of the present invention would proceed as follows. About every week the user employs a prescribed amount of solid-form, chlorine-source tablets or sticks in an erosion device. Coupled with this is the periodic addition of the glycoluril-source composition, also preferably at weekly intervals. The presence of the glycoluril prolongs the useful life of the chlorine, reducing the frequency with which chlorine would otherwise have to be added.

In an alternate method, the solid-form material includes the chlorine-source composition and glycoluril, for example about 95% TCCA and about 5% glycoluril. This formulation has a slowed erosion rate compared to prior art chlorine products, and therefore will last up to two weeks or more. The stabilizing of the chlorine effected by the glycoluril matches well with the extended erosion life of these alternate tablets or sticks.

In addition, other chemicals may be used at the same time. In particular, it may be desirable to perform periodic "shocking" of swimming pool or other water, a common step in prior art procedures. In this case, the shock may be conveniently performed, for example every two weeks, by adding a conventional material, such as sodium dichlorocyanurate, at the same time as the addition of the glycoluril. A full pool treatment system would then only require the addition of algicide, such as a quaternary ammonium compound, at the same two week interval, thus providing the user with a convenient system and method for the treatment of swimming pool water.

It has been observed that the ratio of glycoluril to total available chlorine can be selected to optimize the duration and microbicidal efficacy of the chlorine. The amount of glycoluril in the water is preferably limited to an extent appropriate to result in sufficient hydrolyzing of the chlorine. It is possible that the presence of too much glycoluril in comparison to the amount of total available chlorine will affect the amount of chlorine in solution, and therefore the microbicidal activity. In a sense, the glycoluril can be present in such high amounts relative to the chlorine that the chlorine is made so stable as to reduce its microbicidal activity. For example, a standard hypochlorite solution will effectively kill $10^6$ bacteria in about 30 seconds. A ratio of glycoluril to total available chlorine of about 5:1 will result in a kill of about half of the bacteria in about two minutes, and higher ratios will further delay the kill time. Therefore, although water systems having higher ratios of glycoluril to total available chlorine will still have microbicidal efficacy, the performance will be diminished. It has been found that preferred ratios of total available chlorine to glycoluril are from about 10:1 to about 1:10, more preferably about 5:1 to about 1:5. While increased stability of chlorine is normally associated with decreased microbicidal activity, the present invention provides increased stability and desired microbicidal activity.

The present invention is useful in a wide variety of applications. A person skilled in the art can readily determine the suitability of given chlorine-source and glycoluril-source compositions for a particular aqueous system. The present invention may also be used in conjunction with a variety of other chemicals such as algicides, fungicides, clarifiers, pH adjusters, sequesterants and the like, and may be used with other chlorine stabilizers such as cyanuric acid, oxazolidinone, imidazolidinone, dimethylhydantoin, succinimide, toluenesulfonamide, sulfonamidobenzoic acid, melamine, dioxohexahydrotriazine, piperazinedione, and azodicarbonamidine.

In addition to the stabilization of chlorine, the present invention has also been found to provide several ancillary benefits to the aqueous systems. For example, the addition of glycoluril in the amounts indicated reduces the offensive chloramine odor associated with certain chlorinating systems, such as those using TCCA. Similarly, the development of trihalomethanes is diminished in the presence of the glycoluril.

In one aspect of the present invention, objectionable compounds and odors in aqueous systems are inhibited by maintaining concentrations of 1–100 ppm cyanuric acid (1–40 ppm preferred), 1–100 ppm glycoluril (preferred 5–20) and 1–5 ppm available chlorine in the water. The chlorine is provided by a compressed form of trichloro-s-triazinetrione which also contains up to about 50% glycoluril. This compressed source of available chlorine has the unique property of dissolving appreciably slower than compressed 100% trichloro-s-triazinetrione. In addition, the glycoluril in the water greatly stabilizes the chlorine in the system.

The compositions and methods of the present invention permit an easier swimming pool sanitation program when compared to traditional pool chlorine treatments. First, since the chlorine has a much longer life in water, less total chlorine is required to operate the pool. Second, since less chlorine is needed, a slower dissolving form of chlorine may be used. Thus, fresh compressed chlorine additions to a skimmer or an erosion control device need to be made only infrequently, making it possible to be gone for a minimum of 2 weeks without getting algae, cloudy water or other water problems. A person may simply add the compressed chlorine (with glycoluril) to the skimmer or chlorinator, and set the time clock to operate the pump and filter for the prescribed hours each day.

As with other chlorination treatments, the treatment of the present invention anticipates a superchlorination or other "shock" treatment to remove inorganic and organic materials. With the present invention, this may be accomplished with peroxymonopersulfate in lieu of chlorine.

Glycoluril at the preferred levels improves the odor of swimming pool water due to reduced formation of inorganic chloramines, organic chloramines and other odorous organic chlorides. Pools treated as described herein also have less tendency to have acid pH drift, further inhibiting the formation of odorous and irritating chloramines. It is to be appreciated that the present invention aids in reducing pool odors regardless of whether the chlorine used is inorganic hypochlorite (calcium, lithium, sodium or potassium) or organic (trichloro-s-triazinetrione or sodium dichloro-s-triazinetrione).

The following Examples further illustrate the present invention, and are provided as exemplary but not restrictive as to the scope of the present invention.

EXAMPLE 1

This Example illustrates a method for treatment of water systems in accordance with the present invention. This experiment was conducted to demonstrate the rate of loss of chlorine from solutions containing cyanuric acid, glycoluril and mixtures of the two. This experiment was conducted under controlled conditions designed to simulate conditions expected while operating a pool under full sunlight.

Four liter beakers containing 3500 ml of distilled water were placed in a Revco environment chamber equipped with a special ultra violet lamp that emits UV radiation at 295–340 nm. It is known that chlorine is degraded by sunlight in the region of 295–340 nm. The water was balanced to the following specifications:

| | |
|---|---|
| Calcium Hardness | 200–250 ppm |
| Total Alkalinity | 100–135 ppm |
| pH | 7.2–7.4 |

The test chemicals were then added as shown in Table I below:

TABLE I

| | Test Chemical Systems | |
|---|---|---|
| Beaker #1 | Cyanuric Acid (CYA) (ppm) | Glycoluril (G) (ppm) |
| 1 | 10 | 0 |
| 2 | 50 | 0 |
| 3 | 0 | 5 |
| 4 | 0 | 10 |
| 5 | 0 | 20 |
| 6 | 50 | 5 |
| 7 | 10 | 5 |
| 8 | 50 | 10 |
| 9 | 10 | 10 |
| 10 | 50 | 20 |
| 11 | 10 | 20 |

The chlorine source for this study was trichloro-s-triazinetrione (TCCA). The chlorine demand on the test systems was met by adding excess chlorine and allowing the water to circulate overnight. The total available chlorine level was adjusted the next morning with the LiOCl stock solution.

The study was conducted over a 24 hour period, during which the beakers were stirred continuously. The test solutions were exposed to the ultraviolet radiation at 295–340 NM. The air and water temperatures were controlled at 80°–85° F., and the relative humidity at 80–100%. Water samples were taken and the total available chlorine was measured using a HACH 3000 spectrophotometer and DPD colorimetric method. Due to the large number of beakers involved, the study was conducted in two runs.

TABLE II

| | Test Data - Run #1 | | | | |
|---|---|---|---|---|---|
| Beaker # | 1 | 2 | 3 | 4 | 5 |
| CYA/G (ppm) | 10/0 | 50/0 | 0/5 | 0/10 | 0/20 |
| Time | $TCl_2$ | $TCl_2$ | $TCl_2$ | $TCl_2$ | $TCl_2$ |
| Initial | 1.80 | 1.78 | 1.79 | 1.82 | 1.80 |
| 1 hr | 1.36 | 1.48 | 1.65 | 1.68 | 1.67 |
| 2 hr | 1.08 | 1.25 | 1.54 | 1.56 | 1.53 |
| 3 hr | 0.93 | 1.15 | — | — | — |
| 9 hr | 0.25 | 0.68 | 1.26 | 1.31 | 1.31 |
| 19 hr | 0.09 | 0.27 | 0.95 | 1.01 | 1.01 |
| 24 hr | 0.06 | 0.15 | 0.80 | 0.87 | 0.89 |

TABLE III

| | Test Data - Run #2 | | | | | |
|---|---|---|---|---|---|---|
| Beaker # | 6 | 7 | 8 | 9 | 10 | 11 |
| CYA/G (ppm) | 0/5 | 10/5 | 50/10 | 10/10 | 50/20 | 10/20 |
| Time | $TCl_2$ | $TCl_2$ | $TCl_2$ | $TCl_2$ | $TCl_2$ | $TCl_2$ |
| Initial | 1.50 | 1.51 | 1.52 | 1.53 | 1.60 | 1.5 |
| 2 hr | 1.27 | 1.38 | 1.36 | 1.43 | 1.45 | 1.4 |
| 5 hr | 1.15 | 1.24 | 1.29 | 1.31 | 1.34 | 1.3 |
| 21 hr | 0.89 | 0.82 | 0.94 | 0.98 | 0.98 | 0.9 |
| 24 hr | 0.61 | 0.80 | 0.88 | 0.91 | 0.90 | 0.9 |

The objective of this study was to determine the rate of loss of total available chlorine ($TCl_2$) from water systems containing cyanuric acid, glycoluril and mixtures of the two, when exposed to ultraviolet light in the wavelength region of 295–340 nm. The chlorine half-life was determined by plotting % remaining total available chlorine ($TCl_2$) vs. time (hours). As shown in TABLE IV, water systems containing both cyanuric acid and glycoluril exhibited a greater half-life than water systems that contained only cyanuric acid, i.e., the residual total available chlorine is dissipated more slowly in water systems containing a combination of cyanuric acid and glycoluril, Therefore, the chlorine is available for a longer period of time, and its bactericidal and disinfecting activity is more continuously effective.

TABLE IV

| | Chlorine Half-life | | |
|---|---|---|---|
| Beaker #1 | CYA (ppm) | Glycoluril (ppm) | t ½ (hrs) |
| 1 | 10 | 0 | 5.0 |
| 2 | 50 | 0 | 7.0 |
| 3 | 0 | 5 | 22.0 |
| 4 | 0 | 10 | 24.0 |
| 5 | 0 | 20 | 25.0 |
| 6 | 50 | 5 | 29.0 |
| 7 | 10 | 5 | 27.0 |
| 8 | 50 | 10 | 33.0 |
| 9 | 10 | 10 | 35.0 |
| 10 | 50 | 20 | 32.0 |
| 11 | 10 | 20 | 35.0 |

EXAMPLE 2

Solutions comprising 1 ppm, 2.5 ppm, and 5 ppm total available chlorine from TCCA, and glycoluril concentrations of 5, 10 and 25 ppm, were tested for biocidal activity. The compositions were added to the test microbes and kill rates were measured. It was determined that each of the chlorine concentrations had greater biocidal activity at lower glycoluril concentrations. Additionally, the rate of biocidal activity in the solution of 25 ppm glycoluril was slower than the rates at 5 and 10 ppm glycoluril.

EXAMPLE 3

This Example examines the potential for glycoluril to build up through normal swimming pool usage. A 20,000 gallon vinyl in-ground pool was filled with water and balanced to the following specifications:

| | |
|---|---|
| Calcium Hardness: | 175 ppm |
| Total Alkalinity: | 125 ppm |
| pH: | 7.4 |
| CYA: | 35 ppm |

The pool was maintained at 1 to 3 ppm total available chlorine using compressed, one-half pound TCCA sticks, and was shocked biweekly using lithium hypochlorite to bring the total available chlorine level to 8 ppm.

During the eight month test period the glycoluril level ranged from 1 to 5 ppm. A sum of 1125 grams of glycoluril was added to the pool during the test period. At the end of the test period less than 1 ppm of glycoluril was measured in the water.

EXAMPLE 4

This Example illustrates the ability of glycoluril to reduce the volatility of chlorine and inorganic chloramines from aqueous systems, thereby reducing the offensive odors caused by the compounds. The results indicate that the glycoluril appears to effectively retard the loss of free chlorine and inorganic chloramines from aqueous systems.

To determine the effect of glycoluril upon the volatility of chlorine and chloramines, a conventional airstripping apparatus was constructed. Air was initially passed through a wad of glass wool to trap solid particles, as well as oil droplets. Next, the air went through a column filled with activated carbon to further clean the air stream. After the carbon filter, another glass wool wad trapped any carbon particles that may have escaped the column. Sequential filtering such as this has been previously shown to generate halogen demand free air.

Demand free air was channeled into a sparging tank filled with demand free water. Air leaving the tank should have been saturated with water. This water rich air was used to strip chlorine from the solutions used in the subsequent experiments. It was necessary to use water saturated air for these experiments to minimize evaporative losses in the flasks containing the halogen solutions. Moreover, to increase the effect of the air stripping action, magnetic stirrers were used to continually agitate the solutions.

Chlorine was dosed into Erlenmeyer flasks containing one liter of demand free water (18 megohm resistance) at a concentration of 2 ppm. Ammonium chloride concentration was 2 ppm. Glycoluril was added to give a final concentration of 1.2 or 5 ppm. Flask 1 contained chlorine and 5 ppm glycoluril, flask 2 contained chlorine and the ammonium salt, flask 3 contained chlorine, the ammonium salt and 1.2 ppm glycoluril, and flask 4 contained chlorine, the ammonium salt and 5 ppm glycoluril. In flasks 3 and 4, the ammonium chloride was added after the addition of the chlorine and glycoluril. The results are shown in Table V and in FIG. 1.

FIG. 1 shows the results of the experiment with concentrates of glycoluril of 1.2 and 5.0 ppm. It is apparent that the addition of glycoluril to chlorine in Flask #1 was able to dramatically slow the volatilization of chlorine. In the presence of ammonia, 1.2 ppm glycoluril reduced the chloramine volatilization slightly. At 5 ppm glycoluril in the presence of ammonia, the chloramine volatilization was reduced to a greater extent.

TABLE V

| Flask | Total Halogen ppm |
|---|---|
| *Time = 0* | |
| 1 | 2.01 |
| 2 | 1.96 |
| 3 | 2.00 |
| 4 | 1.99 |
| *Time = 15 hr* | |
| 1 | 1.96 |
| 2 | 1.16 |
| 3 | 1.10 |
| 4 | 1.46 |
| *Time = 19 hr* | |
| 1 | 1.90 |
| 2 | 1.03 |
| 3 | 0.98 |
| 4 | 1.43 |

EXAMPLE 5

A further study was conducted to demonstrate the efficacy of chlorine as a disinfectant when stabilized with glycoluril alone or with glycoluril and another chlorine stabilizer. It was shown that a solution containing 1.5 mg/l total available chlorine remains essentially equally efficacious as a disinfectant, whether combined with 7 mg/l of glycoluril alone, or with 7 mg/l glycoluril and 50 mg/l isocyanuric acid (CYA). Glycoluril used in accordance with the present invention at varying concentrations, as previously discussed, is an effective stabilizer for the chlorine disinfectant and the chlorine remains an effective disinfectant, either in the presence or absence of other chlorine stabilizers.

EXAMPLE 6

The following Example illustrates the effectiveness of glycoluril to inhibit the formation of trihalomethanes (THM) from humic acid. Test solutions were prepared in new 120 ml vaccine bottles which were washed with chromic acid cleaning solution, rinsed in hot tap water, and then in distilled water before use. The following stock solutions were prepared for use in these tests: a 200 ppm solution of available chlorine from commercial bleach, a 0.1% humic acid solution (Humic acid (HA), sodium salt; Aldrich Chemical Co., Inc., CAS #1415-93-6), a 0.04% glycoluril solution, and a 0.1% s-triazinetrione (CYA) solution. Thirteen solutions were prepared as outlined in Table VI.

TABLE VI

| | Preparation of Test Solutions | | | |
|---|---|---|---|---|
| | ml of Test Stock Solution | | | |
| Bottle | HA | Glycoluril | CYA | Chlorine |
| 1 | 0.3 | 1.5 | — | 6 |
| 2 | 0.3 | 3.0 | — | 6 |
| 3 | 0.3 | 7.5 | — | 6 |
| 4 | 0.3 | 15.0 | — | 6 |

TABLE VI-continued

Preparation of Test Solutions

| | ml of Test Stock Solution | | | |
|---|---|---|---|---|
| Bottle | HA | Glycoluril | CYA | Chlorine |
| 5 | 0.3 | 1.5 | 6 | 6 |
| 6 | 0.3 | 3.0 | 6 | 6 |
| 7 | 0.3 | 7.5 | 6 | 6 |
| 8 | 0.3 | 15.0 | 6 | 6 |
| 9 | 0.3 | — | — | 6 |
| 10 | 0.3 | — | 6 | 6 |
| 11 | — | 15.0 | — | 6 |
| 12 | — | — | 6 | 6 |
| 13 | — | — | — | 6 |

Each bottle was ¾ filled with boiled distilled water, and the stock solutions were then added thereto. Each bottle was then filled to the top with boiled distilled water, covered with a TEFLON® cap, and sealed with a metal vaccine crimp cap. The bottles were held at room temperature overnight and the next day were analyzed for the presence of trihalomethanes. The solutions were analyzed for chloroform, bromoform, bromodichloromethane and dibromochloromethane, and the results are shown in Tables VII and VIII.

TABLE VII

Concentrations of Reactants in Solutions and the Resulting ppm Chloroform Assayed in each Solution

| | ml of Test Stock Solution | | | | Results |
|---|---|---|---|---|---|
| Bottle | HA | Glycoluril | CYA | Chlorine | (ppm (CHCl3) |
| 1 | 15 | 5 | — | 10 | 0.015 |
| 2 | 15 | 10 | — | 10 | <0.010 |
| 3 | 15 | 25 | — | 10 | 0.061 |
| 4 | 15 | 50 | — | 10 | 0.102 |
| 5 | 15 | 5 | 50 | 10 | 0.069 |
| 6 | 15 | 10 | 50 | 10 | 0.047 |
| 7 | 15 | 25 | 50 | 10 | 0.030 |
| 8 | 15 | 50 | 50 | 10 | 0.031 |
| 9 | 15 | — | — | 10 | 0.137 |
| 10 | 15 | — | 50 | 10 | 0.081 |
| 11 | — | 15 | — | 10 | 0.088 |
| 12 | — | — | 50 | 10 | 0.059 |
| 13 | — | — | — | 10 | <0.010 |

TABLE VIII

Percent Reduction of Chloroform in Sample Compared to the Control, Solution 9, at 137 ppb

| Bottle | ppb CHCl₃ | % Reduction in THM |
|---|---|---|
| 1 15HA, 5G* | 15 | 89.1 |
| 2 15HA, 10G | <10 | >92.7 |
| 3 15HA, 25G | 61 | 55.5 |
| 4 15HA, 50G | 102 | 25.5 |
| 5 15HA, 5G, 50CYA | 69 | 49.6 |
| 6 15HA, 10G, 50CYA | 47 | 65.7 |
| 7 15HA, 25G, 50CYA | 30 | 78.1 |
| 8 15HA, 50G, 40CYA | 31 | 77.4 |
| 9 positive control | 137 | — |
| 10 15HA, 50CYA | 81 | 40.9 |
| 11 50G | 88 | 35.8 |
| 12 50CYA | 59 | 56.9 |
| 13 negative control | <10 | >92.7 |

*G = Glycoluril

As the data reveals, except for chloroform, the THMs were below the minimum detection level of less than 0.010 ppm in all test solutions. Solution 13 was a negative control, containing only 10 ppm chlorine in boiled distilled water, and it had less than 0.010 ppm chloroform. When CYA alone (#12), glycoluril alone (#11) and CYA plus glycoluril together (#10) were added to the chlorine solution, there were increases in chloroform to 59, 88 and 81 parts per billion (ppb), respectively. This indicated that available chlorine reacted with these compounds or impurities in these compounds to form some chloroform. The addition of only humic acid to the chlorine solution (#9) gave the highest reading for chloroform of 137 ppb, and acted as the positive control.

Solutions 1–4 represented varying concentrations of glycoluril in combination with 15 ppm humic acid and chlorine. The results indicate that 5 and 10 ppm glycoluril almost completely prevented chloroform formation, while 25 ppm only inhibited formation by 55.5%, and 50 ppm glycoluril only resulted in 25.5% reduction over the positive control. It is therefore shown that low levels of glycoluril (5 and 10 ppm) prevent chloroform formation from humic acid almost completely, while higher concentrations inhibit THM formation but to a lesser extent. These results are explainable on the assumption that an impurity in the glycoluril resulted in the formation of the chloroform. At 5 and 10 ppm levels, the impurity was too low to form an appreciable amount of chloroform, while at the higher concentrations there was sufficient impurities to appreciably affect the test. In any event, the tests do demonstrate the effectiveness of glycoluril to prevent or inhibit the formation of THMs.

Solutions 5–8 represent varying levels of glycoluril with 50 ppm CYA. This treatment group gave good reduction over the positive control, and the results were consistent with varying concentrations of glycoluril. There was some slight chloroform inhibition at 5 ppm glycoluril and greater inhibition at 10, 25 and 50 ppm glycoluril in combination with the CYA. Maximum inhibition was reached at 25 ppm, with no improvement at 50 ppm. Thus, the optimum glycoluril range may be in the range of 10–40 ppm.

This test amply demonstrates a definite reduction of chloroform from the reaction of chlorine with humic acid when the treatment group contained both CYA and glycoluril. There was about 41% reduction by 50 ppm CYA alone, but as high as 78% reduction was found with combinations of CYA and glycoluril. The combination of CYA and glycoluril was more effective at low concentrations than either compound by itself.

EXAMPLE 7

The following Example demonstrates the prevention of offensive odors due to the creation of simple inorganic chloramines. Two beakers were each filled with 2000 ml distilled water and the pH was adjusted to 7.2. In the first beaker 50 ppm CYA was added along with 10 ppm $TCl_2$ from a TCCA stock solution. The solution was allowed to mix for 10 minutes. In the second beaker 50 ppm of glycoluril was added along with 10 ppm $TCl_2$ from the TCCA stock solution. Again, the solution was allowed to mix for 10 minutes. Ammonium chloride (0.1 g) was added to each beaker and allowed to mix for five minutes. Both solutions were then tested for chloramine odor by a panel of seven people.

All seven people observed chloramine odor in beaker #1. None of the seven observed any chloramine odor in beaker #2.

EXAMPLE 8

The following Example demonstrates the effect of glycoluril and related compounds on the formation of chloramines and chloramine odors from combinations of available chlorine and nitrogen from ammonium chloride. Hard water having 400 ppm calcium and with a pH of 4.0 was used as the diluent in the following tests. Compounds tested included glycoluril (G), dimethylhydantoin (DMH) and 4,4-dimethyl-2-oxazolidinone (DMO) and s-triazinetrione (CYA). Compounds G, DMH, DMO and CYA are commercially available.

A 0.02% available chlorine solution (200 ppm) was prepared by dissolving 0.61 grams of lithium hypochlorite in 1 liter of distilled water. The solution was titrated iodometrically before use in the test. The solution titrated at 0.18%, so 2.2 ml was used in the tests to obtain 20 ppm available chlorine in each test solution.

Fresh 0.04% stock solutions of G, DMO and DMH were prepared in distilled water for these tests.

Test solutions were prepared in PYREX® test tubes and were covered with stainless steel caps between preparation and use in the odor tests. Solutions were tested for odor within three hours of preparation. Solutions were kept at ambient room temperature during preparation and testing.

Nine panelists were asked to smell each test solution and rank them as 0, 1, 2, 3 or 4. Zero was to be used when there was no chloramine odors, 1 if there was a barely detectable odor, 2 if the odor was very distinct but not strong, 3 used for strong chloramine odors, and 4 for odors that were very strong.

A series of test solutions were set up for each test compound as indicated in the following Table.

TABLE IX

Protocol for Preparation of Odor Test Solutions

| Tube | ml diluent | ml 0.04% test cmpd. | ppm test cmpd. | ml 0.02% avail Cl$_2$ | ml 200 ppm NH$_4$Cl |
|---|---|---|---|---|---|
| 1 | 18.4 | 0.25 | 5 | 2.2 | 0.76 |
| 2 | 17.1 | 0.50 | 10 | 2.2 | 0.76 |
| 3 | 17.4 | 1.25 | 25 | 2.2 | 0.76 |
| 4 | 16.1 | 2.5 | 50 | 2.2 | 0.76 |
| 5 | 18.6 | 0 | 0 | 2.2 | 0.76 |
| 6 | 18.6 | 2.5 | 50 | 0 | 0.76 |
| 7 | 18.7 | 2.5 | 50 | 2.2 | 0 |
| 8 | 19.0 | 0 | 0 | 2.2 | 0 |

The ratio of ammonium nitrogen to available chlorine was approximately 1:10, an optimum ratio for the formation of chloramines from ammonium.

The odor score for each test solution was determined by averaging the nine individual panelist scores. Thus, the lowest possible score (no odor) would be 0 and the highest odor score possible would be 4.0 (maximum odor).

Glycoluril reduced odor scores by approximately 50% at 5 and 10 ppm levels and gave odor scores approximating chlorine with no ammonium nitrogen added at 25 and 50 ppm levels. Thus, at 25 and 50 ppm levels chloramine odor formation was apparently eliminated by the compound.

DMH at low levels, 5 and 10 ppm, greatly reduced chloramine odors. However, at the higher levels odors were higher than at lower levels. This is also the only compound tested where the odor score in the combination chlorine plus test compound with no ammonium chloride (tube 7) was higher than the score for chlorine by itself (tube 8). It is known that DMH degrades to form chloramines and chlorimines and the increases in odor detected with DMH are thought to reflect this chemistry.

DMO was ineffective at 5 ppm, showed some reduction at 10 ppm and was very effective at 25 and 50 ppm.

CYA was marginally effective at 5 and 10 ppm and was effective at 25 and 50 ppm. The high odor reading for tube 8, the chlorine control for CYA, is an apparent aberration, possibly due to all error in preparation or a dirty piece of glassware.

The combination of CYA and glycoluril did not exhibit any improvement over the performance of glycoluril alone.

EXAMPLE 9

The following Example is a further demonstration of the effect of glycoluril and related compounds on the formation of chloramines and chloramine odors from combinations of available chlorine and nitrogen from ammonium chloride. Acid cleaned glassware was used in this study. Hard water at 400 ppm calcium and a pH of 4.0 was used as the diluent. Compounds tested included glycoluril (G), dimethylhydantoin (DMH), 3,3,5,5-tetramethyl-2-imidazolidinone (TMI), 4,4-dimethyl-2-oxazolidinone and s-triazinetrione (CYA). All of the compounds tested, except TMI, are commercially available.

Tests were performed in PYREX® test tubes. The concentrations of solutions were as outlined in Table XI. The ratio of nitrogen to chlorine in these tests was 1:10. Nitrogen concentrations were 2 ppm and available chlorine concentrations were 20 ppm.

TABLE X

Odor Scores for Solution Tested

| | | | Score for Test Compound | | | | |
|---|---|---|---|---|---|---|---|
| test | test cmpd. (ppm) | avail. Cl$_2$ (ppm) | N (ppm) | G | DMH | DMO | CYA | CYA + G |
| 1 | 5 | 20 | 2 | 0.8 | 0.8 | 1.6 | 0.9 | 1.2 |
| 2 | 10 | 20 | 2 | 1.0 | 0.8 | 1.3 | 0.8 | 0.8 |
| 3 | 25 | 20 | 2 | 0.4 | 1.3 | 0.2 | 0.2 | 0.6 |
| 4 | 50 | 20 | 2 | 0.3 | 1.3 | 0.0 | 0.3 | 0.6 |
| 5 | 0 | 20 | 2 | 1.9 | Positive control | | | |
| 6 | 50 | 0 | 2 | 0.0 | Negative control | | | |
| 7 | 50 | 20 | 0 | 0.2 | 1.7 | 0.8 | 0.6 | 0.3 |
| 8 | 0 | 20 | 0 | 0.9 | Chlorine control | | | |

CYA + G contained 50 ppm CYA and the amount of glycoluril shown in column 2.

TABLE XI

General Protocol for Preparation of Odor Test Solutions

| Tube | ml diluent | ml 0.04% test cmpd.* | ml 0.02% avail. Cl$_2$ | ml 200 ppm NH$_4$Cl |
|---|---|---|---|---|
| 1 | 17.00 | 0.25 | 2 | 0.75 |
| 2 | 16.75 | 0.50 | 2 | 0.75 |
| 3 | 16.00 | 1.25 | 2 | 0.75 |
| 4 | 14.75 | 2.50 | 2 | 0.75 |
| 5 | 15.52 | 2.50 | 2 | 0 |
| 6 | 18.00 | 0 | 2 | 0 |
| 7 | 20.00 | 0 | 0 | 0 |
| 8 | 17.50 | 0 | 2 | 0.75 |

*A = compound G
B = DMH
C = TMI
D = DMO
E = CYA
F = compound G + 50 ppm CYA

The solutions were ranked for odor by a panel of 13 people. The odor score for each test solution was determined by averaging the 13 panelists' scores.

TABLE XII

Odor Scores for Solutions Tested

| | | | Score for Test Compound | | | | | |
|---|---|---|---|---|---|---|---|---|
| Avail. Cl | ppm test cmpd. | ppm N | G | DMH | TMI | DMO | CYA | CYA, G |
| 20 | 5 | 2 | 1.5 | 0.8 | 1.3 | 1.8 | 1.5 | 1.1 |
| 20 | 10 | 2 | 1.1 | 1.1 | 0.5 | 1.8 | 1.6 | 0.9 |
| 20 | 25 | 2 | 1.3 | 0.8 | 0.4 | 1.2 | 0.9 | 0.4 |
| 20 | 50 | 2 | 0.4 | 0.4 | 0.3 | 1.1 | 1.1 | 0.2 |
| 20 | 50 | 2 | 0.2 | 0.2 | 0.1 | 0.7 | 0.4 | 0.1 |
| 20 | 0 | 0 | 0.8 | Chlorine control | | | | |
| 0 | 0 | 0 | 0.2 | Negative control | | | | |
| 20 | 0 | 2 | 3.0 | Positive control | | | | |

All compounds tested inhibited the formation of strong chlorinous odors when ammonium nitrogen was contacted with available chlorine in the ratio 1:10.

At stated ppm, the most effective compounds in odor inhibition in decreasing order of effectiveness were:

5 ppm DMH < CYA, G < TMI < G = CYA < DMO
10 ppm TMI < CYA, G < G = DMH < CYA < DMO
25 ppm TMI = CYA < DMH = CYA < DMO = G
50 ppm TMI = CYA, G < G = DMH < CYA < DMO Some of the compound mixtures with nitrogen had lower odor scores than did chlorine by itself, which averaged 0.85, indicating possible improved odor of chlorine solutions even when no ammonium nitrogen is present.

The utility of these compounds in reducing or even eliminating chlorine odors from aqueous chlorinated systems is apparent from this Example.

EXAMPLE 10

The following Example demonstrates the effect of glycoluril on chlorophenol formation in mixtures of phenol and chlorine. In addition, the effect of glycoluril source compositions on the formation of chlorophenol odors is demonstrated herein.

It is reported that chlorophenols have a threshold odor detection level of 1–3 ppb, whereas chlorine and chloramines have threshold odor detection levels of approximately 0.15–0.65 ppm. This difference in odor detection levels allows for dilutions of reaction mixtures to track the formation of chlorophenols. In this study it was assumed that the detection level was 3 ppb in order to provide an analytical tool.

Chlorine solutions of approximately 100 ppm available chlorine were prepared in distilled water from the following compositions: trichloro-s-triazinetrione (TCCA) and lithium hypochlorite (LiOCl). Solutions containing the following in distilled water were prepared:

TABLE XIII

| Tube # | ppm phenol | ppm G | ppm avail. Cl$_2$* |
|---|---|---|---|
| 1 | 0 | 0 | 10 |
| 2 | 5 | 0 | 10 |
| 3 | 0 | 10 | 10 |
| 4 | 5 | 10 | 10 |
| 5 | 0 | 5 | 10 |
| 6 | 5 | 5 | 10 |
| 7 | 5 | 10 | 5 |
| 8 | 5 | 5 | 5 |
| 9 | 5 | 0 | 5 |
| 10 | 5 | 10 | 0 |
| 11 | 0 | 0 | 10 |
| 12 | 5 | 0 | 10 |
| 13 | 0 | 10 | 10 |
| 14 | 5 | 10 | 10 |
| 15 | 0 | 5 | 10 |
| 16 | 5 | 5 | 10 |
| 17 | 5 | 10 | 5 |
| 18 | 5 | 5 | 5 |
| 19 | 5 | 0 | 5 |
| 20 | 5 | 10 | 0 |

*In tubes 1–10 the chlorine source was LiOCl
In tubes 11–20 the source of chlorine was TCCA The solvents were prepared on day one and the tubes were covered with PARAFILM® and held for two days at room temperature. Dilutions were then made in distilled water. Dilutions were made to obtain 1/25, 1/50, 1/100, 1/200, +e,fra 250+ee , 1/500, 1/1000 and 1/1250 dilutions of each reaction mixture. To arrive at a ppb chlorophenol the highest dilution that each panelist discerned the odor of chlorophenols was multiplied by 3 ppb (the threshold odor concentration). There were seven panelists used and the results of the odor tests are shown in Table XIV below.

TABLE XIV

Chlorophenols Detected in Various Solutions By a Panel of 7 People

| TREAT # | A | B | C | D | E | F |
|---|---|---|---|---|---|---|
| Source of Cl | LI | LI | LI | LI | LI | LI |
| Cl, ppm | 10 | 10 | 10 | 5 | 5 | 5 |
| Phenol, ppm | 5 | 5 | 5 | 5 | 5 | 5 |
| G, ppm | 0 | 10 | 5 | 10 | 5 | 0 |
| Chlorophenol, ppb | 7500 | 3400 | 5100 | 1500 | 2700 | 2600 |

| TREAT # | G | H | I | J | K | L |
|---|---|---|---|---|---|---|
| Source of Cl | TC | TC | TC | TC | TC | TC |
| Cl, ppm | 10 | 10 | 10 | 5 | 5 | 5 |
| Phenol, ppm | 5 | 5 | 5 | 5 | 5 | 5 |
| G, ppm | 0 | 10 | 5 | 10 | 5 | 0 |
| Chlorophenol, ppb | 650 | 350 | 325 | 175 | 175 | 250 |

LI = lithium hypochlorite
TC = trichloro-s-triazinetrione

Lithium hypochlorite generated large quantities of chlorophenolic odorous compounds compared to trichloro-s-triazinetrione. Glycoluril in the range of 5–10 ppm reduced the formation of chlorophenols by a factor of 40–60% in both the LI and TC treatment groups.

The reported detection levels for chlorophenols are 1–3 ppb. The ppb chlorophenols were determined by taking the highest dilution of chemical mixture where a chlorophenol odor could be detected and multiplying this factor by 3 ppb (the minimum detectable level). The results reported are an average of the observations for each of the six people used in the odor detection panel.

Glycoluril effectively reduced the formation of chlorophenols from phenol in the presence of 5 or 10 ppm available chlorine from an inorganic chlorine donor (lithium hypochlorite) and an organic, halamine (trichloro-s-triazinetrione).

This Example shows the ability of glycoluril to inhibit the formation of odorous, chlorinous by-products in aqueous systems. It also illustrates the ability of glycoluril to reduce the formation of TOX (total organic halides) since chlorophenols are one example of such chemicals.

EXAMPLE 11

This Example is a further demonstration of the effect of glycoluril and related compounds on odor formation from mixtures of phenol and chlorine.

Chlorine solutions of 200 ppm available chlorine were prepared in distilled water from CHLOROX® bleach (sodium hypochlorite). Solutions were prepared in acid cleaned tubes and were covered with parafilm and held for two days at room temperature. Dilutions were then made in distilled water to obtain 1/25, 1/50, 1/100, 1/250, 1/500, 1/1000, 1/2500, 1/5000 and 1/10000 dilutions of each reaction mixture. To arrive at ppb chlorophenol in reaction mixtures, the highest dilution at which each panelist discerned the odor of chlorophenols was multiplied by 3 ppb (the threshold odor concentration). There were 10 panelists. A summary of the solutions tested and the results of the odor tests are shown in Table XV below.

rine from solutions. In addition, chloramine volatility is effectively reduced.

To determine the effect of glycoluril upon the volatility of chlorine and chloramines, the airstripping apparatus of Example 4 was used. Air from an in-house air line initially passed through glass wool to trap solid particles and oil droplets. Next, the air went through a column filled with activated carbon to further clean the air stream. More glass wool was then used to trap any carbon particles that may have escaped the column. Sequential filtering such as this is known to generate halogen demand free air.

Demand free air was channeled into a sparging tank filled with demand free water. Air leaving the tank was accordingly saturated with water. This water-rich air was used to strip chlorine from the solutions used in the experiments. It was necessary to use water-saturated air to minimize evaporative losses in the flasks containing the halogen solutions. Magnetic stirrers were used to continually agitate the solutions and increase the effect of the airstripping action.

Chlorine was dosed into three flasks containing one liter of demand free water (18 MΩ resistance) at a concentration of approximately 2 ppm. Ammonium chloride was added to two flasks at a concentration of 2 ppm. Glycoluril was added to one flask to give a final concentration of 5 ppm. In each case, flask 1 contained chlorine only, flask 2 contained chlorine and the salt, and flask 3 contained chlorine, the ammonium salt and glycoluril. In flask 3, the ammonium chloride was added after the addition of the chloride and the glycoluril.

Figure 2:
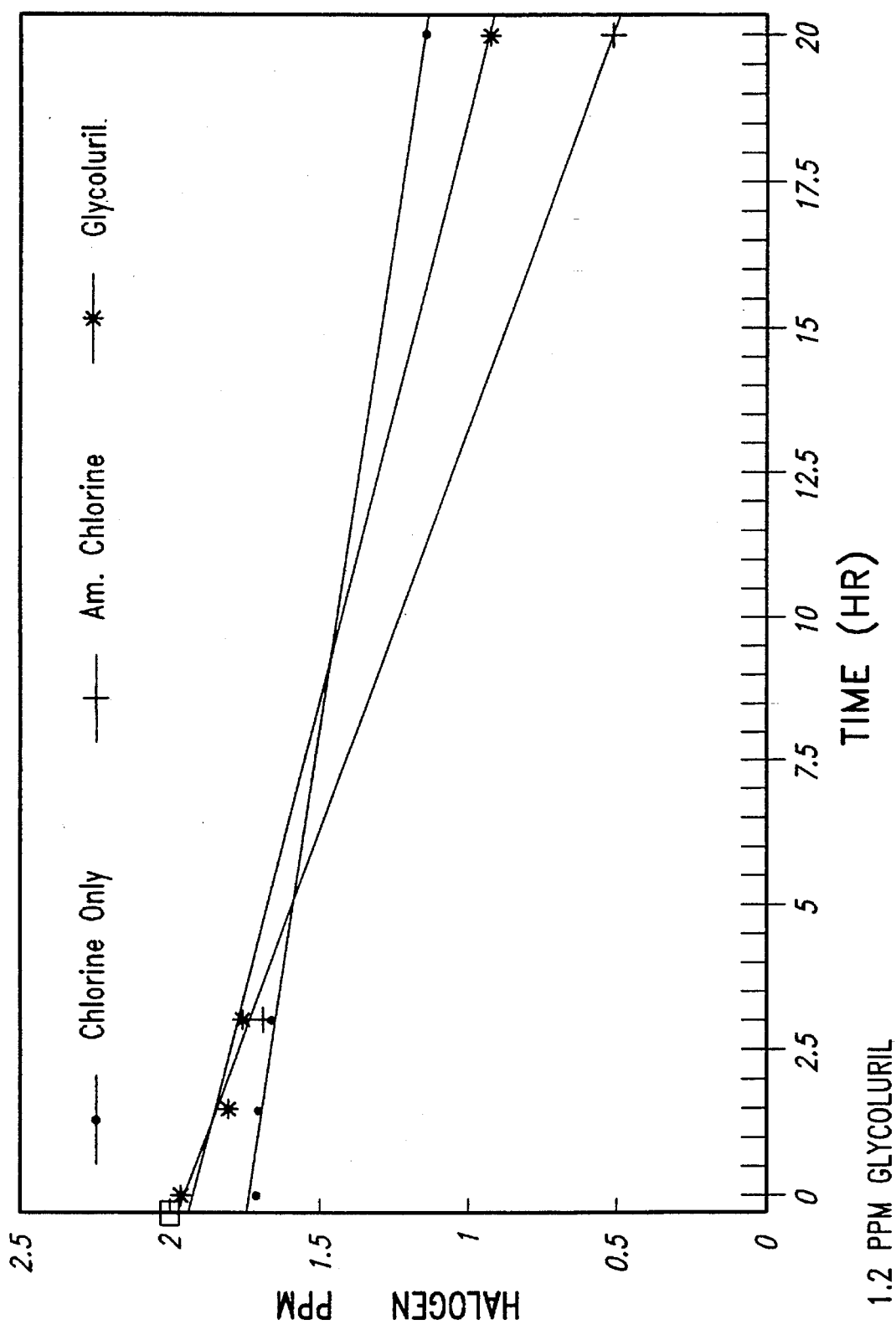
FIG. 2 shows chloramine volatility over time when 1.2 ppm glycoluril is added to a chlorine-containing media.

FIG. 2 shows the results of an experiment when glycoluril was added at a concentration of 1.2 ppm. As can be seen from the regressed data, flask 1: $r^2=0.99$, slope=−0.03; flask 2: $r^2=0.99$, slope=−0.07; and flask 3: $r^2=0.99$, slope=−0.05. Based on this data, glycoluril reduces the rate of chloramine volatility by about 29%.

Figure 3:
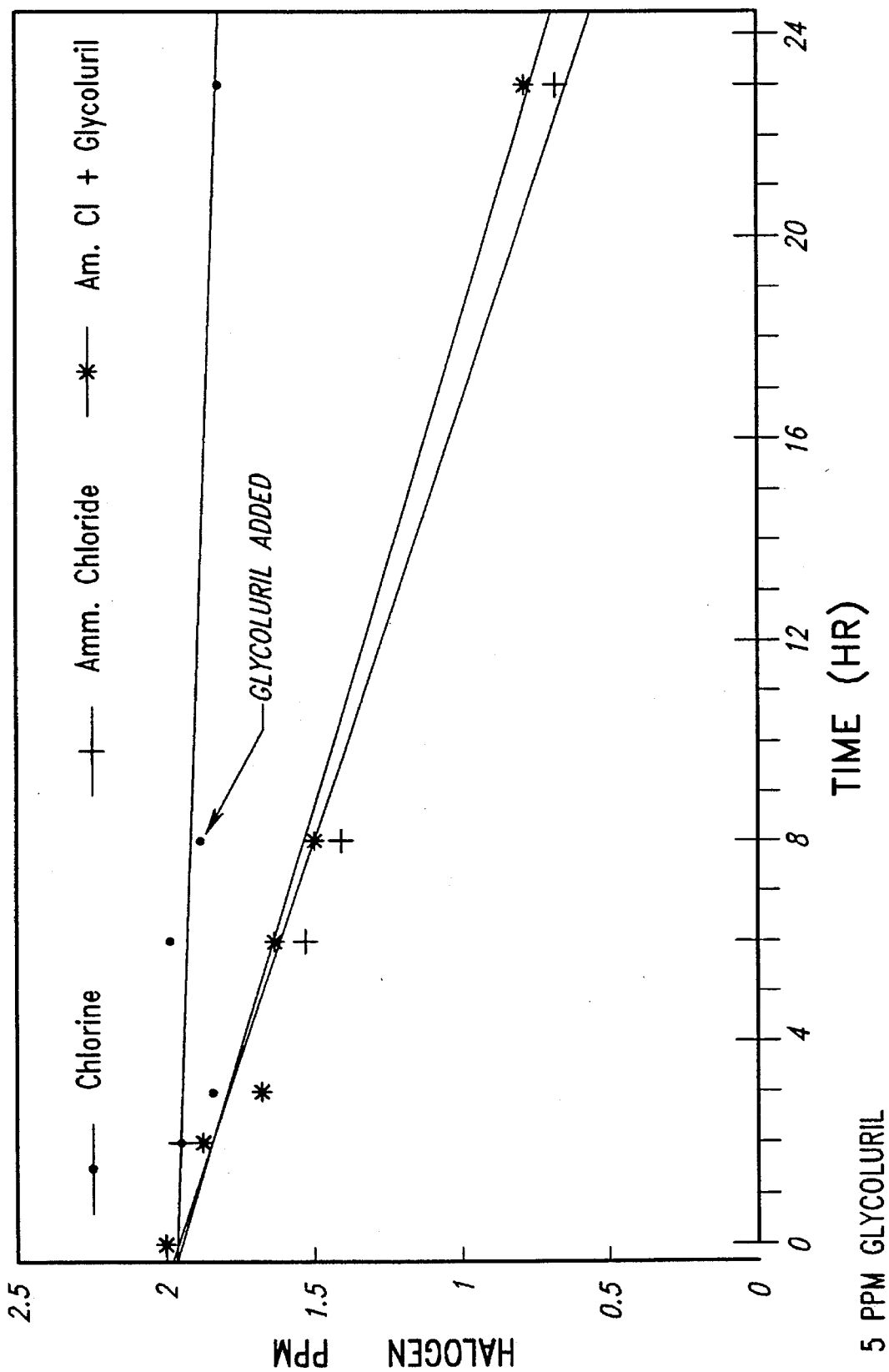
FIG. 3 shows chloramine volatility over time when glycoluril is added at a 5.0 ppm concentration level.

As shown in FIG. 3, when the concentration of glycoluril was 5 ppm the effect upon chloramine volatility in the

TABLE XV

Chlorophenols Detected in Various Solutions By a Panel of 10 People

| ppm phenol | ppm cmpd. | ppm $Cl_2$ | Average Odor Scores phenol cmpd. | | | | | |
|---|---|---|---|---|---|---|---|---|
| | | | G | DMH | TMI | DMO | CYA | CYA, G |
| 50 | 10 | 20 | 12075 | 12487 | 8632 | 13200 | 15225 | 8415 |
| 50 | 25 | 20 | 10755 | 9135 | 6645 | 10680 | 12300 | 8280 |
| 0 | 25 | 20 | 0 | negative control | | | | |
| 50 | 0 | 20 | 19500 | positive control | | | | |

In spite of the high levels of chlorine and phenol used, these compounds noticeably reduced odors caused by chlorophenols. TMI by itself was the most effective single compound. Surprisingly, the combination CYA and G gave improved results over either compound alone. Of the commercially available compounds, the CYA/glycoluril combination was superior to any of the commercially available compounds.

Since a primary use of glycoluril will be with chlorinated isocyanurates in pools, spas and other circulating water systems, the superior ability of this combination to combat both due to chloramines and odorous organic halides, such as chlorophenols, is both surprising and fortuitous.

EXAMPLE 12

The ability of glycoluril to inhibit the volatilization of chlorine and chloramines was also tested. The results indicate that glycoluril effectively retards the loss of free chlopresence of ammonium chloride was about 17%. Flask 2: $r^2=0.98$, slope=−0.06. Flask 3: $r^2=0.98$, slope=−0.05. Also, the addition of glycoluril to flask 1 was able to dramatically slow the volatilization of chlorine.

Figure 4:
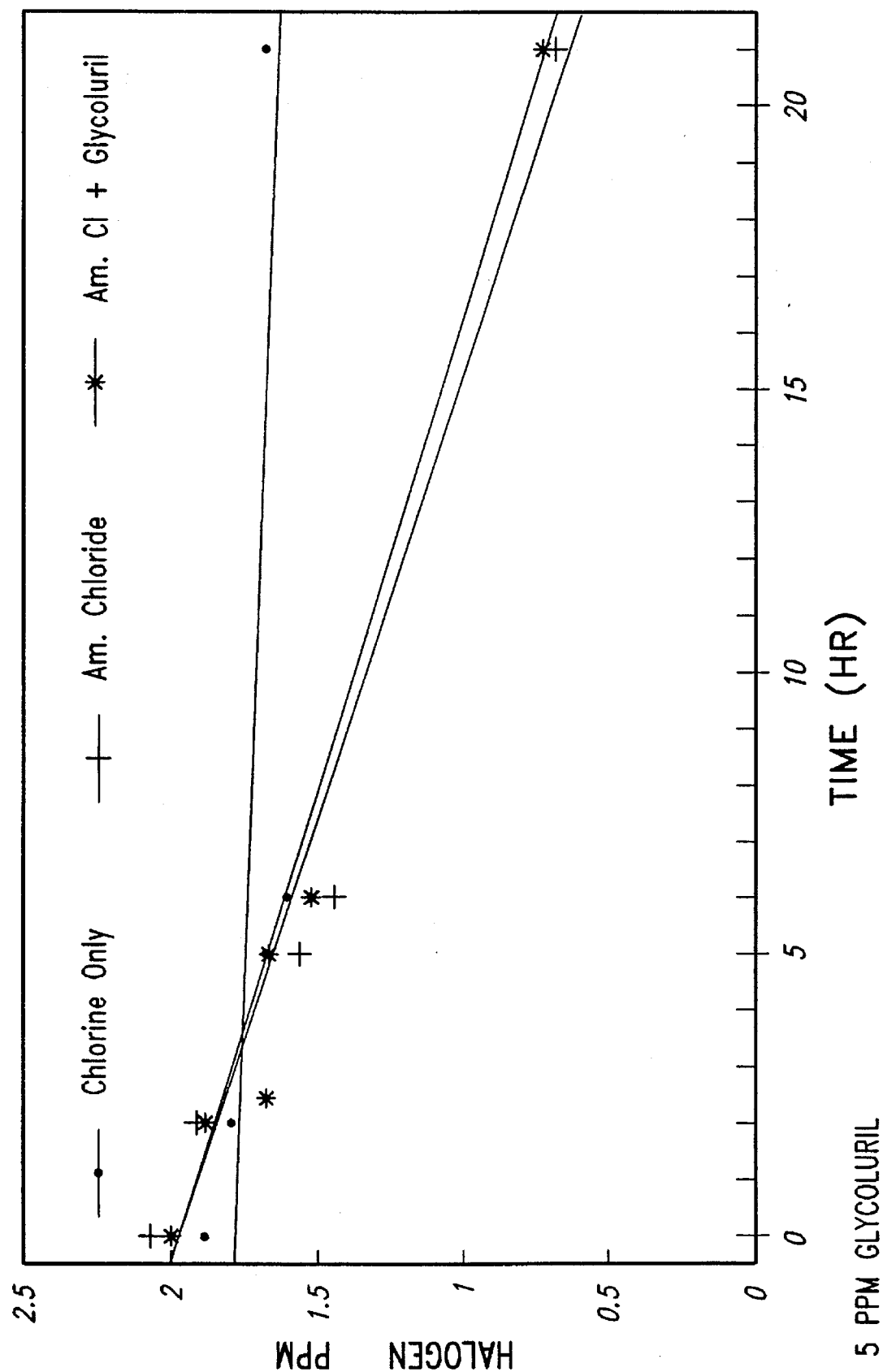
FIG. 4 is another example of chloramine volatility over time when glycoluril is added at a 5.0 ppm concentration level.

FIG. 4 shows the results from a repetition of the previous experiment. Based on the slopes of the regressed data, the difference in chloramine volatility in the presence of glycoluril was about 5%. Flask 2: $r^2=0.96$, slope=−0.063. Flask 3: $r^2=0.99$, slope=−0.06.

Figure 5:
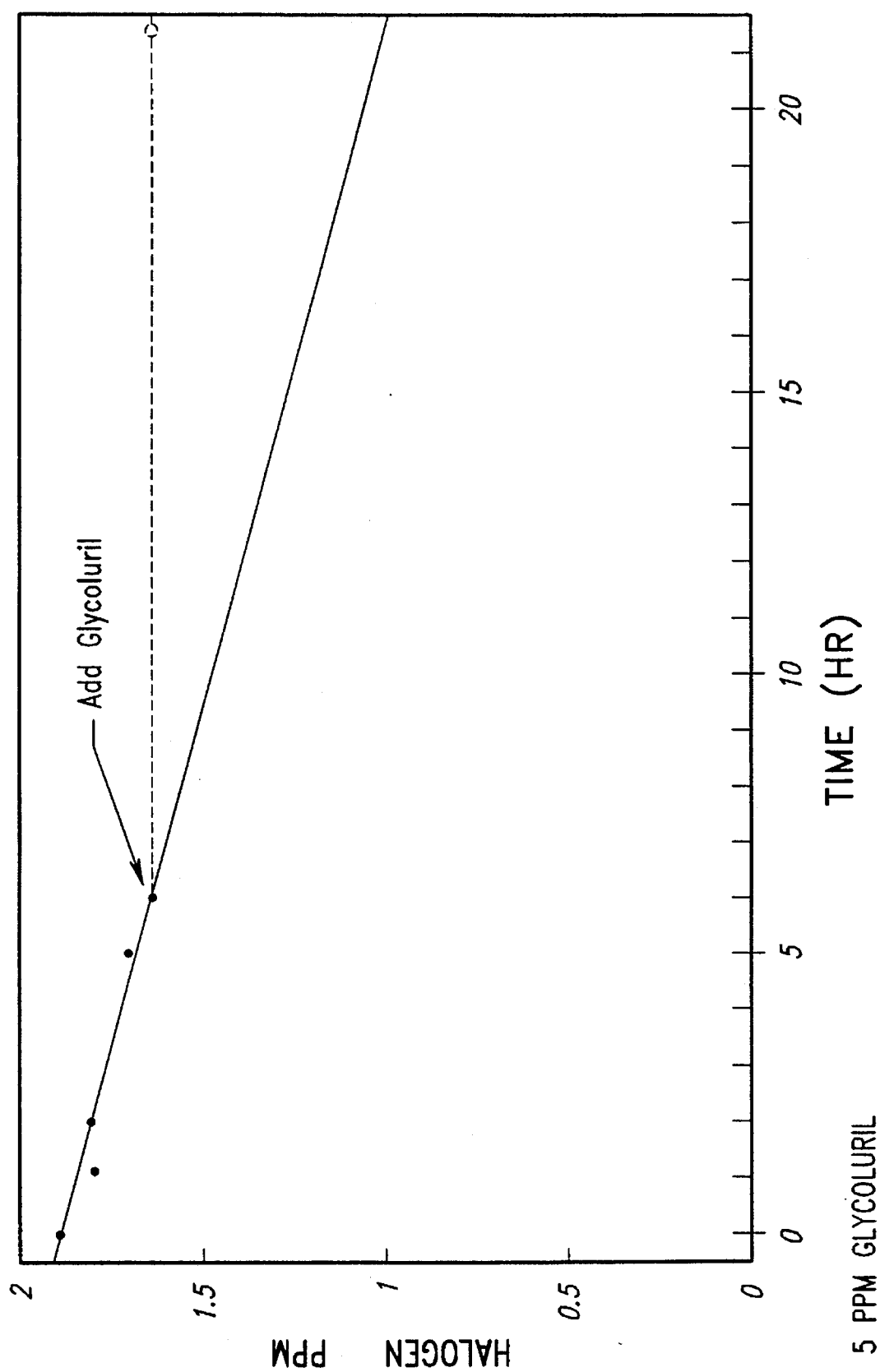
FIG. 5 shows chloramine volatility over time when 5.0 ppm glycoluril is added to a chlorine-only flask at t=6 hours.

As shown in FIG. 5, adding glycoluril to flask 1 decreased the volatility of chlorine as was observed in the previous experiment. The solid line shows the first six hours of data extrapolated to the 21st hour. This approximates the rate of volatilization of chlorine under experimental conditions. The dashed line demonstrates the effect of glycoluril. Glycoluril was added at the sixth hour and chlorine flashoff essentially ceased.

| | Halogen ppm | | |
|---|---|---|---|
| Time (hr) | Flask 1 | Flask 2 | Flask 3 |
| Data for FIG. 3 | | | |
| 0 | 1.70 | 1.97 | 1.96 |
| 1.5 | 1.70 | 1.81 | 1.80 |
| 3 | 1.66 | 1.68 | 1.76 |
| 19 | 1.15 | 0.52 | 0.93 |
| Data for FIG. 4 | | | |
| 0 | 2 | 2 | 2 |
| 2 | 1.92 | 1.94 | 1.86 |
| 3 | 1.83 | 1.69 | 1.68 |
| 6 | 1.98 | 1.51 | 1.62 |
| 8 | 1.88 | 1.42 | 1.52 |
| 23 | 1.82 | 0.67 | 0.77 |
| Data for FIG. 5 | | | |
| 0 | 1.89 | 2.08 | 2.01 |
| 2 | 1.80 | 1.92 | 1.90 |
| 5 | 1.70 | 1.59 | 1.68 |
| 6 | 1.63 | 1.47 | 1.55 |
| 21 | 1.69 | 0.75 | 0.71 |

While the invention has been illustrated and described in detail in the foregoing Examples and description, the same are to be considered as illustrative and not restrictive in character, it being understood that only the preferred embodiment has been shown and described and that all changes and modifications that come within the spirit of the invention are desired to be protected.

What is claimed is:

1. A method for inhibiting the formation of chloramines in aqueous media treated with a chlorine-source disinfectant, which method comprises adding to the aqueous media an amount of unsubstituted glycoluril sufficient to inhibit the formation of chloramines in the aqueous media; wherein said amount of unsubstituted glycoluril is further sufficient to maintain a concentration of from about 1 ppm to about 100 ppm of glycoluril in the aqueous media.

2. The method of claim 1 and which comprises maintaining between about 1 ppm and about 40 ppm glycoluril in the water.

3. The method of claim 2 and which comprises maintaining between about 5.0 and about 20.0 ppm glycoluril in the water.

4. The method of claim 1 in which the glycoluril has the formula:

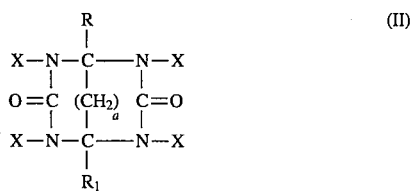

(II)

in which R and R$_1$ are both hydrogen; each X is hydrogen; and a is either 0 or 1.

5. The method of claim 1 and which further includes maintaining in the water a concentration of from about 1 ppm to about 5 ppm available chlorine.

6. The method of claim 5 and which further includes maintaining in the water a concentration of from about 1 ppm to about 100 ppm cyanuric acid.

7. The method of claim 6 and which further includes maintaining in the water a concentration of from about 1 ppm to about 40 ppm cyanuric acid.

8. The method of claim 5 and which comprises adding to the water a first composition comprising a chlorine-source composition, and adding to the water a second composition different from the first composition and comprising unsubstituted glycoluril.

9. The method of claim 8 in which said second composition consists essentially of the unsubstituted glycoluril.

10. The method of claim 8 in which said chlorine-source composition comprises a composition selected from the group consisting of: calcium hypochlorite, sodium hypochlorite, lithium hypochlorite, sodium dichloro-s-triazinetrione, chlorine gas, potassium dichloro-s-triazinetrione, trichloro-s-triazinetrione, bromochlorodimethylhydantoin, dichlorodimethylhydantoin and hypochlorous acid.

11. The method of claim 8 in which said chlorine-source composition is physically combined with said unsubstituted glycoluril and said adding comprises simultaneously adding both compositions to the water.

12. The method of claim 8 in which said chlorine-source composition is physically separate from said unsubstituted glycoluril and said adding comprises separately adding said chlorine-source composition and said unsubstituted glycoluril.

13. The method of claim 8 in which said adding of the chlorine-source composition comprises providing a solid-form material containing the chlorine-source composition, contacting the water with the solid-form material in a manner to effect erosion of the solid-form material, and gradually eroding the material to introduce the chlorine-source composition into the water.

14. The method of claim 8 in which said adding of the unsubstituted glycoluril comprises broadcasting the unsubstituted glycoluril into the water.

15. A method for inhibiting the formation of trihalomethanes in aqueous media treated with a chlorine-source disinfectant, which method comprises adding to the aqueous media an amount of unsubstituted glycoluril sufficient to maintain a concentration of from about 1 ppm to about 100 ppm of glycoluril to inhibit the formation of trihalomethanes in the aqueous media.

16. The method of claim 15 and which comprises maintaining between about 1 ppm and about 40 ppm glycoluril in the water.

17. The method of claim 16 and which comprises maintaining between about 5.0 and about 20.0 ppm glycoluril in the water.

18. The method of claim 15 in which the glycoluril has the formula:

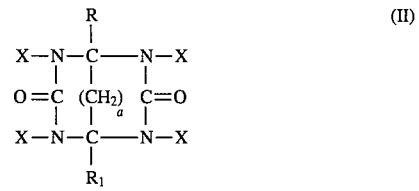

(II)

in which R and R$_1$ are both hydrogen; each X is hydrogen; a is either 0 or 1.

19. A method for inhibiting the formation of chloramine and/or chlorophenol odors in aqueous media treated with a chlorine-source disinfectant, which method comprises adding to the aqueous media an amount of unsubstituted glycoluril sufficient to maintain a concentration of from about 1 ppm to about 100 ppm of glycoluril to inhibit the formation of chloramine and/or chlorophenol odors in the aqueous media.

20. The method of claim 19 and which comprises maintaining between about 1 ppm and about 40 ppm glycoluril in the water.

21. The method of claim 19 and which comprises maintaining between about 5.0 and about 20.0 ppm glycoluril in the water.

22. The method of claim 19 in which the glycoluril has the formula:

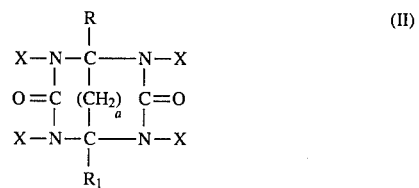

in which R and $R_1$ are both hydrogen; each X is hydrogen; and a is either 0 or 1.

* * * * *

UNITED STATES PATENT AND TRADEMARK OFFICE
CERTIFICATE OF CORRECTION

PATENT NO. : 5,614,528
DATED : March 25, 1997
INVENTOR(S) : Ronald L. Jones et al.

It is certified that error appears in the above-identified patent and that said Letters Patent is hereby corrected as shown below:

In col. 10, line 42, please change the first comma to a period.

In col. 16, line 22, please change "all" to --an--.

In col. 18, lines 36 and 37, please change "+e,fra 250 tee" to --1/250--.

In col. 22, line 64, please add --and-- after second occurrence of "hydrogen;".

Signed and Sealed this

Nineteenth Day of August, 1997

Attest:

BRUCE LEHMAN

Attesting Officer

Commissioner of Patents and Trademarks